United States Patent [19]

Sakakura et al.

[11] Patent Number: 5,252,766
[45] Date of Patent: Oct. 12, 1993

[54] METHOD FOR PRODUCING POLYSILANES

[75] Inventors: Toshiyasu Sakakura; Masato Tanaka; Toshiaki Kobayashi, all of Tsukuba, Japan

[73] Assignee: Director-General of Agency of Industrial Science, Tokyo, Japan

[21] Appl. No.: 759,908

[22] Filed: Sep. 13, 1991

[30] Foreign Application Priority Data

Sep. 14, 1990 [JP] Japan .................................. 2-245122

[51] Int. Cl.$^5$ ............................................... C07F 7/08
[52] U.S. Cl. ..................................... 556/430; 423/324; 423/345; 423/347
[58] Field of Search ................. 556/430; 423/345, 347, 423/324

[56] References Cited

U.S. PATENT DOCUMENTS

| 4,900,861 | 2/1990 | Yokoyama et al. | 556/430 |
| 4,965,386 | 10/1990 | Watson et al. | 556/430 |
| 5,087,719 | 2/1992 | Tilley et al. | 556/430 |

OTHER PUBLICATIONS

J. F. Harrod (ACS Symposium Series 360:89-100 (1988)).
Nakano et al., (Chemistry Letters pp. 83-86, 1989).

Primary Examiner—Paul F. Shaver
Attorney, Agent, or Firm—Birch, Stewart, Kolasch & Birch

[57] ABSTRACT

There is disclosed a method for producing a polysilane which comprises reacting a hydrosilane compound in the presence of an organolanthanoid complex.

12 Claims, No Drawings

METHOD FOR PRODUCING POLYSILANES

FIELD OF THE INVENTION

The present invention relates to a method for producing polysilanes.

Polysilanes are useful compounds whose applications, for example, as a raw material for silicon carbide, a photoresist raw material, an electroconductive material, a thermochromic material, and a nonlinear optical material, are expected to expand.

BACKGROUND OF THE INVENTION

Conventionally, polysilanes are synthesized by using as a raw material a silicon compound having chlorine atoms and carrying out the Wurtz-type condensation reaction in the presence of an alkali metal. However, in such a process for the synthesis of polysilanes, the reaction proceeds violently and thus it is difficult to control. In addition it is required to use an alkali metal, whose risk of ignition is high and whose handling is difficult, in an amount of at least twice as much as the mol of the silane compound monomer. Further, a trace amount of chlorine remains in the produced polysilane, leading to such problems as lowering of the electroconductivity.

In relation to the above, recently processes for the synthesis of polysilanes are suggested wherein a hydrosilane is subjected to dehydrogenative condensation in the presence of a complex of a transition metal, such as rhodium, iridium, ruthenium, palladium, platinum, cobalt, nickel, titanium, zirconium, and hafnium (described in, for example, Japanese Patent Application (OPI) No. 198631/1989; *Chemistry Letters*, 1989, page 83; and *ACS Symposium Series*, Vol. 360, page 89, 1988, published by the American Chemical Society). However, there are still problems that, for example, the catalyst activity is low and the amounts of by-products are large, and therefore it cannot be said that these processes are industrially satisfactory processes. On the other hand, in recent years, attempts to use, instead of a transition metal complex catalyst, a complex of lanthanoid metals in a catalytic reaction are being energetically made. However, only a few reactions are reported wherein the catalyst activity is recognized such reactions as for hydrogenation and ethylene polymerization.

SUMMARY OF THE INVENTION

Therefore, the object of the present invention is, taking the above into consideration, to provide a method for producing a polysilane by developing a polysilane synthesis catalyst system that uses a hydrosilane as a raw material and is high in activity and selectivity.

The above and other objects, features, and advantages of the invention will become apparent from the following detailed description.

DETAILED DESCRIPTION OF THE INVENTION

The above object of the present invention has been attained by providing a method for producing a polysilane, comprising subjecting a hydrosilane compound to dehydrogenative condensation in the presence of lanthanoid complex as a catalyst.

As the central metal of the lanthanoid complex used as a catalyst in the present invention, an arbitrary metal can be selected from the group consisting of lanthanoid elements (i.e., lanthanum, cerium, praseodymium, neodymium, promethium, samarium, europium, gadolinium, terbium, dysprosium, holmium, erbium, thulium, ytterbium, and lutetium). Among them, lanthanum, neodymium, samarium, ytterbium, and lutetium are preferably used, and more preferably neodymium is used.

As the ligand of the lanthanoid complex used as a catalyst in the present invention, for example, halogen, hydrogen, alkyl, aralkyl, aryl, alkylsilyl, arylsilyl, olefin, diene, triene, tetraene, cyclodiene, cyclotriene, cyclotetraene, allyl, alkoxy, aryloxy, alkylthio, arylthio, cyclopentadienyl, alkylamine, arylamine, pyridyl, alkylphosphine, arylphosphine, alkylarylphosphine, alkylisocyanido, arylisocyanido, or ether can be used, which may be substituted. Particularly preferable ligands are a hydrogen atom, an alkyl group (preferably having 1 to 10 carbon atoms, e.g., methyl, trimethylsilylmethyl, bis(trimethylsilyl)methyl, ethyl, i-propyl, t-butyl, neopentyl, and hexyl), pentamethylcyclopentadienyl, and tetrahydrofuran. The lanthanoid complex is preferably an organolanthanoid complex.

As the structure of the metal complex used in the present invention as a catalyst, one represented by the following formula (I) or (II), or their associated substance is particularly preferable, but the invention is not restricted to them.

Formula (I)

$Cp^*_2LnR$

Formula (II)

$Cp^*_2Ln'$ wherein Cp* represents a cyclopentadienyl group or a substituted cyclopentadienyl group, Ln represents any lanthanoid metal, Ln' represents samarium, europium, or ytterbium, and R represents hydrogen, a monovalent organic group, or a monovalent silyl group. As a preferable monovalent organic group represented by R, methyl, trimethylsilyl, bis(trimethylsilyl)methyl, neopentyl, phenyl, and benzyl can be mentioned.

The hydrosilane compound used in the present invention can be represented by the following formula (III), (IV), or (V):

Formula (III)

$R^1R^2SiH_2$

Formula (IV)

$HR^1R^2Si\text{-}(A)_n\text{-}SiR^3R^4H$

Formula (V)

$H_2R^1Si\text{-}B\text{-}SiR^2H_2$ wherein $R^1$, $R^2$, $R^3$, and $R^{4'}$, which may be the same or different, each represent a hydrogen atom, a halogen atom, or a hydrocarbon group, A represents a substituted or unsubstituted silylene group, B represents a divalent organic group, and n is 0 or a positive integer. More particularly, $R^1$, $R^2$, $R^3$, and $R^4$ each represent a hydrogen atom, a halogen atom (e.g., F, Cl, and Br), a hydrocarbon group, such as an alkyl group (preferably having 1 to 10 carbon atoms, e.g., methyl, ethyl, propyl, i-propyl, butyl, t-butyl, and hexyl), an aryl group (preferably having 6 to 15 carbon atoms, e.g., phenyl, 1- naphthyl, and p-tolyl), and a group (e.g., benzyl); A represents a substituted silylene group, such as SiMe$_2$, SiHMe, and SiHPh; and B represent a divalent group, for example, such as p-phenylene, m-phenylene, o-phenylene, methylene, ethylene, and trimethylene.

As the hydrosilane compound, specifically tetrahydrosilane, methylsilane, ethylsilane, n-hexylsilane, phenylsilane, dimethylsilane, diethylsilane, diphenylsilane, hexahydrodisilane, 1,2-diphenyldisilane, 1,2-dimethyldisilane, and 1,4-bis(silyl)benzene can be mentioned. Among them, tetrahydrosilane, methylsilane, n-hexylsilane, phenylsilane, hexahydrodisilane, and 1,4-bis(silyl)benzene are preferably used.

The polysilane synthesis reaction in the presence of the above lanthanoid complex is preferably carried out under the following reaction conditions.

The reaction temperature is about $-50°$ to $300°$ C., generally about $20°$ to $200°$ C., preferably about $20°$ to $160°$ C.

In the reaction, although a solvent is not necessarily needed, an aromatic compound such as toluene and benzene, an ether such as diethyl ether, tetrahydrofuran, and dioxane, or an aliphatic hydrocarbon, such as pentane, hexane, and decane, can be used.

The metal complex as a catalyst is used in an amount of 0.0001 to 0.5 mol, preferably 0.001 to about 0.05 mol, per mol of the hydrosilane compound.

The product is readily separated by removing low-boiling compounds from the reaction mixture followed, for example, by reprecipitation or gel filtration.

The synthesis reaction may be carried out at an atmospheric pressure in the case of the hydrosilane compound being a liquid, and at a pressure in the range of 1 to 100 atmospheric pressure in the case of the hydrosilane compound being a gas. The reaction time may be 1 hour to several tens of days, generally several hours to several days.

The polysilane obtained by the present method comprises, as a basic skeleton, a structure represented by the following formulae (A) and/or (B):

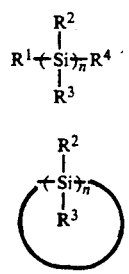

Formula (A)

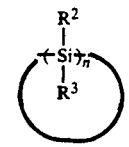

Formula (B)

wherein each of $R^1$ to $R^4$, have the same meaning as defined above, and n is an integer of 2 or over. With respect to n, there is no upper limit, but it is preferably 2 to 100,000, more preferably 2 to 10,000, most preferably 2 to 5,000. The polymerization degree of polysilane to be produced may be selected according to the purpose for use, and generally the higher the polymerization degree, the more preferable for practical use. In order to produce a polysilane having a high molecular weight, a higher reaction temperature and/or a longer reaction time are effective. When the product according to the present invention is the mixture of a chain-type polysilane and a cyclic-type polysilane, the mixture as it is can be adopted for various usage.

In the present polysilane synthesis reaction, without using any alkali metal, a polysilane can be obtained in a high yield from a hydrosilane using as a catalyst a lanthanoid complex under mild conditions near room temperature, whose industrial meaning is very significant.

The present invention will now be described more specifically based on Examples.

Example 1

A solution of bis(phentamethylcyclopentadienyl)-(bis(trimethylsilyl)methyl)neodymium (0.026 mmol) in phenylsilane (1.0 ml, 8.04 mmol) was stirred at $80°$ C. for 2 days under a nitrogen atmosphere. Unreacted phenylsilane and low-boiling products were removed under reduced pressure ($30°$ C., 5 mmHg), to obtain a very viscous oil (820 mg) of a polysilane. The values of the physical properties of the thus obtained polysilane are given below:

IR (neat) 2104 cm$^{-1}$ ($\nu_{Si-H}$) 916 cm$^{-1}$ ($\delta_{Si-H}$)

The absorbance ratio of $\delta_{Si-H}$ to $\nu_{Si-H}$: 0.51

$^1$H-NMR (CDCl$_3$) $\delta$ 6.5-8.0 (br. m, Ph), 3.8-5.3 (br. m, SiH). The integral ratio of Ph to SiH: about 5. FAB-MS (matrix: metanitrobenzyl alcohol). A parent ion was not observed, and a number of fragment peaks, wherein the strength gradually decreased from the region where the mass number was 100 or over were observed.

Typical peaks are shown below: m/e (relative intensity) 478 (Ph$_4$Si$_6$H, 8), 449 (Ph$_4$Si$_5$H, 18), 421 (Ph$_4$Si$_4$H, 15), 373 (Ph$_3$Si$_5$H$_2$, 20), 343 (Ph$_3$Si$_4$, 27), 315 (Ph$_3$Si$_3$, 20), 287 (Ph$_3$Si$_2$, 20), 266 Ph$_2$Si$_4$, 18), and 259 (Ph$_3$Si, 100).

Average molecular weight (GPC): 600.

Example 2

When hydrobis(pentamethylcyclopentadienyl)-neodymium (0.01 mmol) and phenylsilane (1.0 mmol) were stirred at room temperature under a nitrogen atmosphere, bubbles of hydrogen were released violently. After the stirring was continued for 1 day under the same conditions, unreacted phenylsilane and low-boiling products were removed under reduced pressure ($30°$ C., 5 mmHg) to obtain a polysilane having the same physical properties as those in Example 1.

Examples 3 to 7

Polysilanes shown in Table 1 were obtained quantitatively by stirring bis(pentamethylcyclopentadienyl)-(bis(trimethylsilyl)methyl)neodymium (0.01 mmol) and phenylsilane (1.0 ml, 8.04 mmol) in a nitrogen atmosphere under respective conditions as shown in Table 1.

TABLE 1

| Example | Condition | Product | Mw | Mw/Mn |
|---|---|---|---|---|
| 3 | Room temperature, 15 days | oil | 520 | 1.26 |
| 4 | 80° C., 2 days | gum | 780 | 1.37 |
| 5 | 100° C., 2 days | gum | 990 | 1.54 |
| 6 | 130° C., 2 days | solid | 1600 | 1.91 |
| 7 | 130° C., 2 days, and then 160° C., 7 days | solid | 4380 | 3.09 |

Examples 8 and 9

Polysilanes shown in Table 2 were obtained by replacing phenylsilane to hexylsilane (1 ml, 6.16 mmol) in Example 3 and under the condition as shown Table 2. FD-MS showed that dimer to pentamer are chain-like structure and hexamer or more are cyclic structure.

TABLE 2

| Example | Condition | Product | Mw | Mw/Mn |
|---|---|---|---|---|
| 8 | 80° C., 2 days | oil | 530 | — |
| 9 | 160° C., 13 days | oil | 950 | 1.25 |

Example 10

In an autoclave made of stainless steel (provided with a glass insert of 37 ml) under a nitrogen atmosphere, bis(pentamethylcyclopentadienyl)-(bis(trimethylsilyl)-methyl)neodymium (31.5 mg, 0.05 mmol) and benzene (2 ml) were included, and tetrahydrosilane (2.0 g, 63 mmol) was supplied at 31 atmospheric pressure and reacted at 100° C. in an oil-bath for 3.5 days. Solvent and low-boiling products were removed under reduced pressure (at room temperature, 0.1 mmHg), to obtain 194 mg of yellow powder of polysilane.

IR (nujol): 2104 cm$^{-1}$, 897 cm$^{-1}$, 855 cm$^{-1}$, 671 cm$^{-1}$.

Example 11

In an autoclave made of stainless steel (provided with a glass insert of 37 ml) under a nitrogen atmosphere, bis(pentamethylcyclopentadienyl)-(bis(trimethylsilyl)-methyl)neodymium (0.05 mmol) and benzene (2 ml) were included, and 1.2 g of hexahyrdodisilane was supplied under pressure and reacted at 100° C. for 2 days and 16 hours. Solvent and low-boiling products were removed under reduced pressure (at room temperature, 0.1 mmHg), to obtain 693 mg of yellow powder of polysilane.

IR (nujol): 2108 cm$^{-1}$, 897 cm$^{-1}$, 857 cm$^{-1}$, 665 cm$^{-1}$.

Example 12

In an autoclave made of stainless steel (provided with a glass insert of 37 ml) under a nitrogen atmosphere, bis(pentamethylcyclopentadienyl)-(bis(trimethylsilyl)-methyl)neodymium (0.05 mmol) and benzene (2 ml) were included, and methylsilane (1.0 g) was supplied under pressure and reacted at 100° C. for 2 days. Solvent and low-boiling products were removed under reduced pressure (at room temperature, 0.1 mmHg), to obtain 604 mg of yellow powder of polysilane.

IR (nujol): 2080 cm$^{-1}$, 1245 cm$^{-1}$, 930 cm$^{-1}$.

Example 13

In an autoclave made of stainless steel (provided with a glass insert of 37 ml) under a nitrogen atmosphere, bis(pentamethylcyclopentadienyl)-(bis(trimethylsilyl)-methyl)neodymium (0.05 mmol) and benzene (2 ml) were included, and methylsilane (1.1 g) was supplied under pressure and reacted at 50° C. for 2 days. Solvent and low-boiling products were removed under reduced pressure (at room temperature, 0.1 mmHg), to obtain 267 mg of a viscous oil product of polysilane.

IR (neat): 2114 cm$^{-1}$, 1249 cm$^{-1}$, 932 cm$^{-1}$.
Mw: 512
Mw/Mn: 1.16

Example 14

In an autoclave made of stainless steel (provided with a glass insert of 37 ml) under a nitrogen atmosphere, bis(pentamethylcyclopentadienyl)-(bis(trimethylsilyl)-methyl)neodymium (0.05 mmol) and benzene (2 ml) were included, and methylsilane (0.9 g) was supplied under pressure and reacted at room temperature for 3.5 days. Solvent and low-boiling products were removed under reduced pressure (at room temperature, 0.1 mmHg), to obtain 281 mg of a viscous oil product of polysilane.

IR (nujol): 2114 cm$^{-1}$, 1249 cm$^{-1}$, 932 cm$^{-1}$.
Mw: 541
Mw/Mn: 1.28

Example 15

Bis(pentamethylcyclopentadienyl)(bis(trimethylsilyl)methyl)neodymium (0.01 mmol) and 1,4-bis(silyl)benzene (3.32 mmol) were reacted for 2 days at 100° C. and under a nitrogen atmosphere. An insoluble polysilane polymer was obtained quantitatively.

IR (nujol): 2120 cm$^{-1}$, 915 cm$^{-1}$

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing a polysilane, which comprises reacting a hydrosilane compound in the presence of a lanthanoid complex, wherein the central metal of said lanthanoid complex is neodymium.

2. The method for producing a polysilane as claimed in claim 1, wherein the reaction of the hydrosilane compound is a dehydrogenative condensation.

3. The method for producing a polysilane as claimed in claim 1, wherein the ligand of the lanthanoid complex is selected from the group consisting of halogen, hydrogen, alkyl, arralkyl, aryl, alkylsilyl, arylsilyl, olefin, diene, triene, tetraene, cyclodiene, cyclotriene, cyclotetraene, allyl, alkoxy, aryloxy, alkylthio, arylthio, cyclopentadienyl, alkylamine, arylamine, pridyl, alkylphosphine, arylphosphine, alkylarylphosphine, alkylisocyanido, and arylisocyanido, which may be substituted.

4. The method for producing a polysilane as claimed in claim 1, wherein the ligand of the lanthanoid complex is selected from the group consisting of a hydrogen atom, an alkyl group, pentamethylcyclopentadienyl, and tetrahydrofuran.

5. The method for producing a polysilane as claimed in claim 1, wherein the lanthanoid complex is a compound represented by the following formula (I) or (II), or their associated substance:

Formula (I)

Formula (II)

wherein Cp* represents a cyclopentadienyl group or a substituted cyclopentadienyl group, Ln represents neodymium, Ln' represents samarium, europium, or ytterbium, and R represents hydrogen, a monovalent organic group, or a monovalent silyl group.

6. The method for producing a polysilane as claimed in claim 1, wherein the hydrosilane compound is selected from the group consisting of compounds represented by the following formulae (III), (IV), and (V):

Formula (III)

Formula (IV)

$$HR^1R^2Si\text{-}(A)_R\text{-}SiR^3R^4H$$

Formula (V)

$$H_2R^1Si\text{-}B\text{-}SiR^2H_2$$

wherein $R^1$, $R^2$, $R^3$, and $R^4$, which may be the same or different, each represent hydrogen, halogen, or a hydrocarbon group, A represents a substituted or unsubstituted silylene group, B represents a divalent organic group, and n is 0 or a positive integer.

7. The method for producing a polysilane as claimed in claim 1, wherein the hydrosilane compound is selected from the group consisting of tetrahydrosilane, methylsilane, ethylsilane, n-hexylsilane, phenylsilane, dimethylsilane, diethylsilane, diphenylsilane, hexahydrodisilane, 1,2-diphenyldisilane, 1,2-dimethyldisilane, and 1,4-bis(silyl)benzene.

8. The method for producing a polysilane as claimed in claim 1, wherein the reaction temperature is about $-50°$ to $300°$ C.

9. The method for producing a polysilane as claimed in claim 1, wherein the reaction temperature is about $20°$ to $200°$ C.

10. The method for producing a polysilane as claimed in claim 1, wherein the solvent to be used in the reaction is selected from the group consisting of toluene, benzene, diethylether, tetrahydrofuran, dioxane, pentane, hexane, and decane.

11. The method for producing a polysilane as claimed in claim 1, wherein the lanthanoid complex is used in an amount of 0.0001 to 0.5 mol per mol of the hydrosilane compound.

12. The method for producing a polysilane as claimed in claim 1, wherein the lanthanoid complex is used in an amount of 0.001 to 0.05 mol per mol of the hydrosilane compound.

* * * * *

UNITED STATES PATENT AND TRADEMARK OFFICE
CERTIFICATE OF CORRECTION

PATENT NO. : 5,252,766

DATED : October 12, 1993

INVENTOR(S) : Toshiyasu SAKAKURA et al

It is certified that error appears in the above-identified patent and that said Letters Patent is hereby corrected as shown below:

On the Title Page, Item [73]:

Change "Director-General of Agency of Industrial Science, Tokyo, Japan" to --Director-General of Agency of Industrial Science & Technology, Tokyo, Japan--

Signed and Sealed this

Nineteenth Day of April, 1994

Attest:

BRUCE LEHMAN

Attesting Officer

Commissioner of Patents and Trademarks